(12) United States Patent
Batiste et al.

(10) Patent No.: US 9,549,808 B2
(45) Date of Patent: Jan. 24, 2017

(54) BYPASS CONFIGURATION AND METHOD OF CONSTRUCTION

(71) Applicants: Stanley Batiste, Granite Bay, CA (US); Steven Achstein, Roseville, CA (US)

(72) Inventors: Stanley Batiste, Granite Bay, CA (US); Steven Achstein, Roseville, CA (US)

(73) Assignee: Stanley Batiste, Granite Bay, CA (US)

( * ) Notice: Subject to any disclaimer, the term of this patent is extended or adjusted under 35 U.S.C. 154(b) by 2 days.

(21) Appl. No.: 14/093,251

(22) Filed: Nov. 29, 2013

(65) Prior Publication Data

US 2014/0142371 A1 May 22, 2014

Related U.S. Application Data

(63) Continuation-in-part of application No. 13/212,129, filed on Aug. 17, 2011, which is a continuation-in-part of application No. 11/977,953, filed on Oct. 26, 2007, now Pat. No. 9,039,758.

(60) Provisional application No. 61/730,991, filed on Nov. 29, 2012, provisional application No. 60/873,788, filed on Dec. 7, 2006.

(51) Int. Cl.
*A61F 2/06* (2013.01)

(52) U.S. Cl.
CPC .... *A61F 2/064* (2013.01); *A61F 2/06* (2013.01)

(58) Field of Classification Search
CPC ............... A61F 2/82; A61F 2/062; A61F 2/06
USPC ............................................. 604/8; 623/1.13
See application file for complete search history.

(56) References Cited

U.S. PATENT DOCUMENTS

| | | | |
|---|---|---|---|
| 5,197,976 | A | 3/1993 | Herweck et al. |
| 5,662,711 | A | 9/1997 | Douglas |
| 6,338,724 | B1 | 1/2002 | Dossa |
| 6,589,278 | B1 | 7/2003 | Harris et al. |
| 7,105,020 | B2 | 9/2006 | Greenberg et al. |
| 7,128,750 | B1 | 10/2006 | Stergiopulos |
| 2001/0004715 | A1* | 6/2001 | Duran et al. ............... 623/23.72 |
| 2002/0058991 | A1* | 5/2002 | Schmitt ........................ 623/1.15 |

* cited by examiner

*Primary Examiner* — Matthew Schall
(74) *Attorney, Agent, or Firm* — Weide & Miller, Ltd.

(57) ABSTRACT

A method for constructing a vascular connector configured to bypass an occluded vessel which comprises a primary graft stem and a venous outflow stem. In general, the primary graft stem accepts a blood flow from an occluded vessel to bypass the occlusion. The venous outflow stem may extend from a wall of the primary graft stem and divert a portion of the blood flow to a native vein or other vessel of the vascular system. This configuration is beneficial in ensuring adequate blood flow at the vascular connector to inhibit the formation of clots and to extend the patency of the vascular connector.

15 Claims, 14 Drawing Sheets

BYPASS CONFIGURATION AND METHOD OF CONSTRUCTION

1. CROSS-REFERENCE TO RELATED APPLICATIONS

This application claims priority to and the benefit of U.S. Provisional Application 61/730,991 and this application also claims priority to and is a continuation-in-part from U.S. application Ser. No. 13/212,129 filed on Aug. 17, 2012 which is a continuation-in-part of U.S. patent application Ser. No. 11/977,953, filed Oct. 26, 2007, which claims priority to U.S. Provisional Patent Application No. 60/873,788 filed Dec. 7, 2006.

BACKGROUND OF THE INVENTION

2. Field of the Invention

The present invention relates to vascular bypass grafts and, in particular, to a method of forming surgically implanted grafts which increase blood flow and reduce clotting and a method for making such grafts.

3. Related Art

Vascular disease is a leading cause of morbidity and mortality in the United States and throughout the world. The causes of vascular disease include diabetes, hypertension, renal failure, and smoking as well as many other etiologies. Vascular disease can affect any blood vessel in the body and commonly involves the coronary arteries, carotid arteries and the arteries of the lower extremities. The disease is caused by cholesterol, plaque, and calcium deposits which cause vascular wall thickening. Vascular wall thickening occludes the afflicted vessels by narrowing them, which reduces or in some cases, completely blocks blood flow.

Vascular disease leads to progressive narrowing of vessels secondary to plaque build-up within the vessel walls. This plaque is initially soft and initially not flow limiting. Eventually the plaque hardens and progressively becomes larger creating narrowing which becomes clinically significant limiting the body's ability to perform the necessary function of the organ or limb involved. For the heart it begins as chest pain on exertion and eventually a myocardial infarction. In the legs the progressive narrow leads to claudication (pain on exertion) and eventually leads to amputation and limb loss.

Vascular disease is currently treated in several different ways. Patients may engage lifestyle changes, changes to diet and exercise, and medical therapies such as cholesterol lowering drugs. However, for some patients, these non-invasive treatments are insufficient and surgical or invasive intervention such as bypass surgery or angioplasty are necessary.

Bypass grafts are used throughout the body to route blood around occluded or highly stenotic vessels secondary to vascular disease. Currently only single lumen, straight bypass grafts are available, whether created from man-made materials or harvested from a patient's body, cadavers or from animals. These straight bypass grafts are attached by a surgeon to a higher pressure, upstream blood vessel to a lower pressure, downstream blood vessel. They are most commonly used in the heart (coronary artery bypass) and in the extremities (peripheral bypass) with utilization in many other vessels less commonly adopted, such as use in the mesenteric arteries which supply the bowel. A bypass graft can connect or be provided in both short and long lengths, such as an axillary-femoral graft which is attached to the arm artery and passes along the lateral aspect of the chest and abdomen and is attached distally to the leg artery. They also can be used to connect from one side of the body to the other as in the Femoral—femoral bypass which attaches to one of the vessels in the groin then passes across the patient's pelvis and at its distal end attaches to the leg artery of the other leg.

All grafts, including grafts made from harvesting a patient's own vein from a donor site have the common problem of failure. Failure occurs when the grafts, through resistance to flow, has clinically significant decrease in blood flow or complete occlusion. The consequence of this is decreased blood flow to the body parts/areas that the bypass graft serves downstream from the graft. For example, a lower extremity bypass failure can lead to ischemia and possible tissue and even limb loss. The reasons for failure are secondary to grafts forming internal clot which ultimately leads to decrease or loss of flow. Blood clotting can occur for many reasons such as slow blood flow, vessel injury, intimal hyperplasia creating occlusion and history of prior clot formation and propagation, and as a result of a patient's increased propensity to form clot. Clotting can occur from one, or a combination of these factors.

A patient undergoing bypass surgery has a bypass graft, surgically implanted. The bypass graft provides a substitute route for blood flow to bypass an occluded region. The bypass graft is a tube structure with two ends. One end attaches on one end before the region of vascular occlusion, and on the other end to the patient's vascular system downstream of the occlusion. In this manner, the bypass graft improves the patient's blood flow around the occlusion.

The majority of bypass grafts function well over time, however, in a significant number of patients the bypass grafts themselves become occluded. Where a bypass graft becomes occluded, the patient must undergo another surgery or intervention to place a second graft or to open and reestablish flow to the original graft.

As a result, there is a need in the art for a bypass graft that can provide a route for blood flow while preventing occlusion which leads to graft failure. The description herein enables such a bypass graft as well as a method of implanting the bypass graft.

BRIEF SUMMARY OF THE INVENTION

A vascular connector for bypassing an occluded vessel, such as a vein or artery, is disclosed herein. The vascular connector has features which help ensure an adequate blood flow through the connector after implantation in a patient's vascular system. This is highly beneficial in that it greatly reduces, if not eliminates, the risk of clots forming within the connector and, accordingly, improves graft patency.

The vascular connector may have various configurations. For example, in one embodiment a vascular connector may comprise a primary graft stem fabricated from a substantially hollow member. The primary graft stem may have a first end and a second end to allow blood flow from a first blood vessel through the primary graft stem. It is noted that one end of the primary graft stem may be tapered such as to increase blood pressure at the tapered end. A venous outflow stem fabricated from a substantially hollow member may extend outward from an opening in the primary graft stem to divert a portion of the blood flow from the primary graft stem to a second blood vessel.

One or more ridges may be at one or both ends of the primary graft stem. Similarly, one or more ridges may be at an outflow end of the venous outflow stem. It is noted that the venous outflow stem may extend beyond the first end of the primary graft stem.

In another embodiment, the vascular connector may comprise a primary stem fabricated from a substantially hollow structure and configured to accept a blood flow from a narrowed vessel to bypass the narrowed vessel. A secondary stem fabricated from a substantially hollow structure having a narrower diameter than the primary stem may extend from a wall of the primary stem. The secondary stem may be configured to accept a portion of the blood flow within the primary stem, and divert the portion of blood flow to another vessel.

Similar to above, at least one end of the primary stem may be tapered. It is noted that the secondary stem may be integrally formed with the primary stem or alternatively be a separate structure attached to the primary stem. A tubular venous outflow limb may be to an outflow end of the secondary stem. The secondary stem may extend from a central portion of the primary stem. Alternatively, the secondary stem extends from a wall of the primary stem at one end of the primary stem.

Various methods of bypassing an occluded vessel are disclosed herein as well. For example, a method of bypassing blood flow through a vessel having an occlusion includes providing a vascular connector having a primary stem and a narrower secondary stem extending from an opening in a wall of the primary stem, connecting a first end of the primary stem to the vessel upstream of the occlusion in the vessel, and connecting a second end of the primary stem to a vascular system downstream of the occlusion in the vessel. An outflow end of the secondary stem may then be connected to another vessel of the vascular system. It is noted that a venous outflow limb may be connected to the outflow end of the secondary stem. The venous outflow limb may connect the secondary stem to the other vessel of the vascular system.

It is noted that connecting the vessel to the first end of the primary stem may comprise inserting a ridged first end of the primary stem into an end of the vessel. It is also noted that the vessel may be an artery of the vascular system while the other vessel is a vein of the vascular system.

Also disclosed herein is a unique method of surgically or otherwise creating the Batiste bypass graft from a patients, cadaver or animal harvested vessel. The method and apparatus disclosed herein solves or reduces clotting as a result of two potential factors, both of which are related to slowing of blood flow through the graft. The various designs disclosed herein establish increased flow through the graft and decreases the rate at which restrictions or blockages will form at the distal aspect of the graft while also maintaining blood flow.

The method can use one, or many harvested vascular segments, whether alone, or in numerous combination with other bypass materials such as cryoveins, biologically crated vessels or a multitude on polymers such as PTFE. Using these materials, or a combination of the materials, a surgeon can construct the Batiste configuration in the operating room or the Batiste design can be performed outside of the operating room at an earlier date, or through a public or private industry.

Disclosed herein is a method for constructing a vascular bypass graft comprising providing a first tubular segment having an internal passage having a diameter configured for fluid flow, the first tubular segment having a distal end and a proximal end. This method providing a second tubular segment having an internal passage configured for fluid flow such that the first tubular segment has a distal end and a proximal end and the second tubular segment has a diameter that is less than a diameter of the first tubular segment. The method also forms an opening near the proximal end of the first tubular segment. Then, this method includes attaching the proximal end of the second tubular segment to cover the opening in the first tubular segment such that the inner passage of the second tubular segment is aligned with the opening to thereby form a fluid pathway from the first tubular segment to the second tubular segment.

In one embodiment this method further comprising aligning the second tubular segment generally parallel to the first tubular segment with the distal end of the first tubular segment pointing in the same general direction as the distal end of the second tubular segment. In one configuration, the opening formed in the first tubular segment has a diameter that is generally matched to the diameter of the second tubular segment. This method may further comprise cutting the proximal end of the second tubular segment at an angle of between zero to 90 degrees to prepare it for connection to the first tubular segment. The completed grafts may be packaged such that the vascular bypass graft in a container containing the vascular bypass graft and preservative solution. The container containing the vascular bypass graft is also frozen or chilled. This method of making the graft may be practiced at a medical lab prior to placement in a patient. In one configuration one or more of the first tubular segments and the second tubular segments are constructed from human or animal donor, bioengineered or derived from polymers.

Also disclosed is a method of constructing a bypass graft comprising harvesting a branched vessel from a vessel donor such that the branched vessel has a central leg, first branch leg and a second branch leg, with each of the central leg, first branch leg and second branch leg having and end and an opening to form a fluid pathway from the primary leg to the first branch leg and from the central leg to the second branch leg. The method also attaches a primary segment to a first branch leg and attaching a venous bypass segment to a first branch leg such that the venous bypass segment is linear and extends in a direction that is less than 90 degrees from a linear direction in which the primary segment extend.

In one embodiment the attaching occurs through sutures. The primary segment and the venous bypass segment may comprise synthetic material. The primary segment and the venous bypass segment may are organic and from a donor and the method may further comprise harvesting the primary segment and the venous bypass segment. In one variation the method further includes attaching a central branch extension to the central leg of the branched vessel to extend the length of the central branch. The method may also further include expanding the bypass graft packaging the bypass graft in a container which may contain a solution, such as saline solution. The graft may be chilled or frozen for use at a later time by a surgeon.

Further objects, features, and advantages of the present invention over the prior art will become apparent from the detailed description of the drawings which follows, when considered with the attached figures.

BRIEF DESCRIPTION OF THE DRAWINGS

The components in the figures are not necessarily to scale, emphasis instead being placed upon illustrating the principles of the invention. In the figures, like reference numerals designate corresponding parts throughout the different views.

DETAILED DESCRIPTION OF THE PREFERRED EMBODIMENTS

In the following description, numerous specific details are set forth in order to provide a more thorough description of the present invention. It will be apparent, however, to one skilled in the art, that the present invention may be practiced without these specific details. In other instances, well-known features have not been described in detail so as not to obscure the invention.

The primary reason for the formation of blood clots in a bypass graft is that the blood flow through the graft is of such low velocity that blood clotting mechanisms are triggered. Regions of low velocity blood flow are common in the body's smaller vessels such as veins and capillaries. Low velocity regions are also found in the transitions between larger vessels, such as arteries, to smaller ones, such as veins or capillaries because the reduction in size reduces flow capacity and thus blood flow velocity is also reduced. Thus, if a bypass graft is attached to a small vessel at its outflow end or in a region of low velocity blood flow, only a small amount of blood at low velocity flows through the graft creating circumstances where blood clots may form within the graft. This will cause occlusion of the graft and eventual graft failure.

In general, a vascular bypass graft which improves blood flow in occluded vascular regions and is itself resistant to occlusion by blood clots is disclosed. The vascular bypass graft disclosed herein has several advantages over known bypass grafts. It maintains a high blood flow velocity in conditions where there would otherwise be a low flow rate through the graft, such as where outflow from the distal vascular bypass graft end is low or reduced. Currently known grafts will not stay un-occluded in these conditions because the slow flow through the graft allows blood clots to develop and occlude the graft eventually rendering it non-functional.

Another advantage of the method and apparatus described herein is that the amount of return flow provided through the venous outflow limb is adjustable. In this way, the vascular bypass graft can be custom configured for a particular patient and/or medical application. One aspect of this adjustability is that it is non-invasive and thus allows modification of the amount of blood flow through the vascular bypass graft in response to the new medical conditions or other factors without the need for further surgery.

Another advantage that the design provides increased flow allowing energy dissipation of each pulse wave that otherwise is absorbed into the distal anastomosis at the graft and native artery interface. This added energy transmitted with current graft design causes an inflammatory response which leads to early stenosis development and hence early graft failure. Lessening this water-hammer (blood-hammer) effect helps maintain graft patency.)

Figure 1:
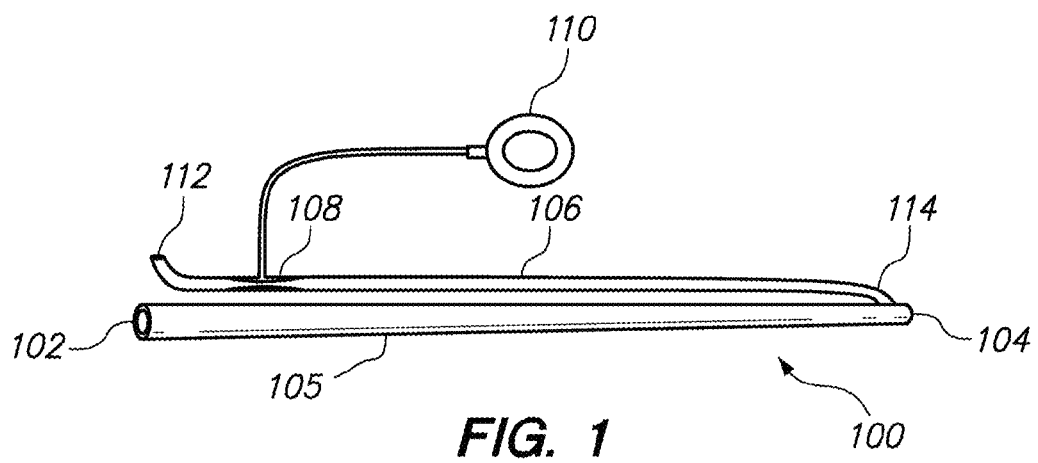
FIG. 1 illustrates an exemplary embodiment of a vascular bypass graft.

Referring now to the drawings, FIG. 1 illustrates an improved vascular bypass graft 100. The vascular bypass graft 100 has a primary member/graft 105, a proximal/first vascular bypass end 102, a distal/second vascular bypass end 104, a venous outflow limb 106, a stenosis restrictor 108, and an optional restrictor controller 110. The venous outflow limb 106 or secondary member has a proximal/first venous end 112 and a distal/second venous end 114. The distal venous end 114 attaches to or is integrally formed adjacent to the distal vascular bypass end 104 such that a flow path is provided that facilitates fluid transmission from the primary graft 105 to the venous outflow limb 106. The vascular bypass graft 100 or any portion thereof can be made in any length to accommodate the need for various vascular systems.

The primary graft 105 is generally a flexible hollow elongate member comprising structure and dimensional configurations to facilitate fluid transmission from the proximal vascular bypass end 102 to the distal vascular bypass end 104. The venous outflow limb 106 is generally a flexible hollow elongate member structured and dimensionally configured to facilitate fluid transmission from the distal venous end 114 to the proximal venous end 112. In one embodiment, the primary graft 105 and venous outflow limb 106 are fabricated from a material that is suitable for surgical implantation into a living organism. The material should be selected for compatibility with living tissue. Such materials include but are not limited to prosthetic polytetraflouroethylen (PTFE) and polyethylene tetraphthlate (Dacron).

In one embodiment, when implanted, the vascular bypass graft 100 is attached to a patient's vascular system at the proximal vascular bypass end 102, the distal vascular bypass end 104, and the proximal venous end 112. In one embodiment, the vascular bypass graft is implanted such that blood flows through the primary graft 105 from the proximal vascular bypass end 102 to the distal vascular bypass end 104. The proximal venous end 112 of the venous outflow limb 106 may be attached to a blood vessel of lower pressure. This attachment of the proximal venous end 112 to a blood vessel of lower pressure ensures that at least a portion of blood in the primary graft 105 flows through the venous outflow limb 106 because fluids, including blood, will naturally flow to a region of lower relative pressure.

The venous outflow limb 106 allows the primary graft 105 to maintain blood flow velocity sufficient to prevent clotting even when the flow velocity would ordinarily be low due to minimal outflow through the distal vascular bypass end 104. Blood flow travels through the primary graft 105 from the proximate vascular bypass end 102 to the distal vascular bypass end 104 with at least a portion of the blood flow diverted through the venous outflow limb 106. This portion of diverted blood flow allows the blood to circulate through the vascular bypass graft 100 at a flow velocity sufficient to prevent clotting even where the patient's vascular system at the distal vascular bypass end 104 has a low blood flow capacity. Thus, the patient's vascular system at the distal vascular bypass end 104 receives its necessary blood flow while the excess blood flow is circulated through the venous outflow limb 106 to a blood vessel of lower pressure to prevent clotting within the vascular bypass graft 100.

The stenosis restrictor 108 controls the amount of blood flow through the venous outflow limb 106 by restricting blood flow through the venous outflow limb 106. The stenosis restrictor 108 can completely restrict (i.e. block) blood flow as well. This control is desirable because it allows the vascular bypass graft 100 to be configured to the needs of each particular patient at a particular time. More specifically, the stenosis restrictor 108 can increase or decrease blood pressure at the distal vascular bypass end by increasing or decreasing the amount of blood flowing through the venous outflow limb 106. Thus, the stenosis restrictor 108 could decrease blood flow through the venous outflow limb to increase blood pressure, for example, to outer extremities or anytime the body requires it such as during physical activity. Conversely, the stenosis restrictor 108 could increase blood flow through the venous outflow limb to decrease blood pressure at the distal vascular bypass end 104 and increase anti-clotting circulation through the vascular bypass graft 100 when such increased blood pressure is not necessary.

In one embodiment, a desired flow condition provides sufficient flow through the primary graft 105 to prevent clotting while still maintaining sufficient pressure at the distal vascular bypass end 104. By selecting the proper stenosis restrictor 108 setting, the pressure and flow rate may be optimized.

The stenosis restrictor 108 may comprise various configurations, devices, or systems that restrict blood flow to achieve operation as described herein including but not limited to balloon or other inflatable devices or other pneumatic or hydraulic systems. In addition, the stenosis restrictor 108 may operate in conjunction with a restrictor controller 110 to variably control the amount of blood flow restriction.

In one embodiment the stenosis restrictor 108 comprises a balloon. In this embodiment, the restrictor controller 110 comprises a pneumatic or hydraulic device for inflating and deflating the balloon to thereby adjust the amount of blood flow restriction. The restrictor controller 110 as a pneumatic or hydraulic device may be configured as a gas or liquid reservoir connected to the stenosis restrictor 108. The amount of blood flow restriction can then be varied by altering the volumetric capacity of the restrictor controller 110 to which the stenosis restrictor 108 is linked. The degree to which the stenosis restrictor 108 restricts blood flow through the venous outflow limb 106 may be substantially proportional and inverse to the volumetric capacity of the restrictor controller 110 of this embodiment.

Figure 2A:
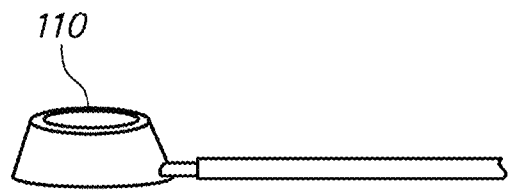
FIG. 2A illustrates a reservoir for a stenosis restrictor of the vascular bypass graft of FIG. 1.
Figure 2B:
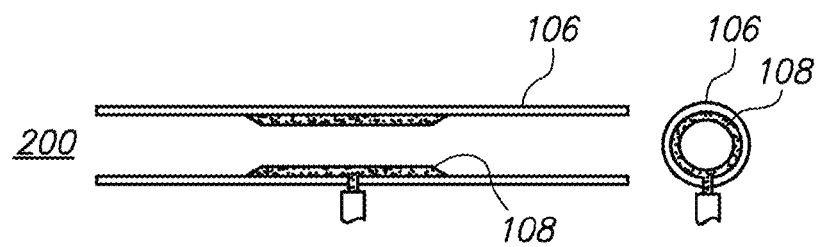
FIG. 2B illustrates a cross-sectional view of a deflated stenosis restrictor of FIG. 1.
Figure 2C:
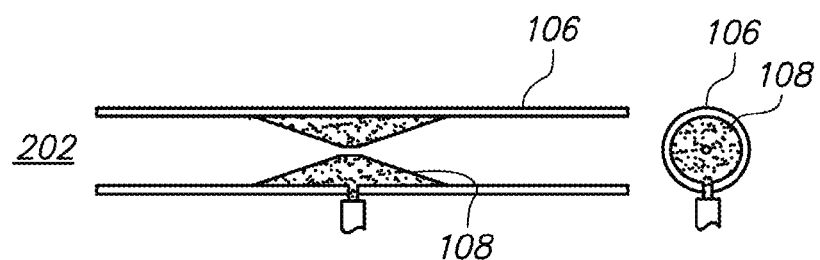
FIG. 2C illustrates a cross-sectional view of an inflated stenosis restrictor of FIG. 1.

The stenosis restrictor 108 and restrictor controller 110 are illustrated in greater detail in FIGS. 2A through 2C. In FIGS. 2B and 2C the stenosis restrictor 108 is shown in both a longitudinal cross-section and a transverse cross-section. Additionally, the stenosis restrictor 108 is depicted in a first deflated state 200 in FIG. 2B and a second inflated state 202 in FIG. 2C. As shown in FIG. 2B, the stenosis restrictor 108 is deflated and provides little resistance to fluid flow within the venous outflow limb 106 thus reducing fluid pressure within the primary graft 105. Conversely, in FIG. 2C, the stenosis restrictor 108 is inflated providing increased resistance to fluid flow within the venous outflow limb 106 thus increasing the overall fluid pressure within the vascular bypass graft.

Figure 3A:
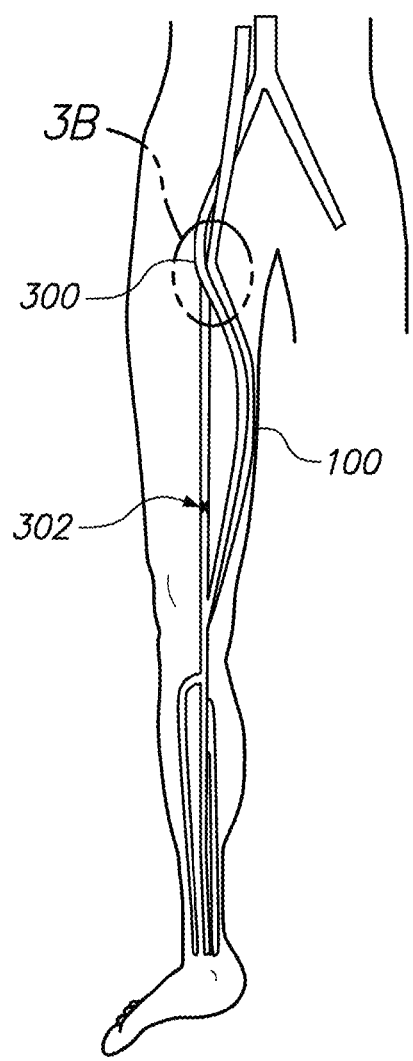
FIG. 3A is a regional view of the proximal connections of the vascular bypass graft of FIG. 1.
Figure 3B:
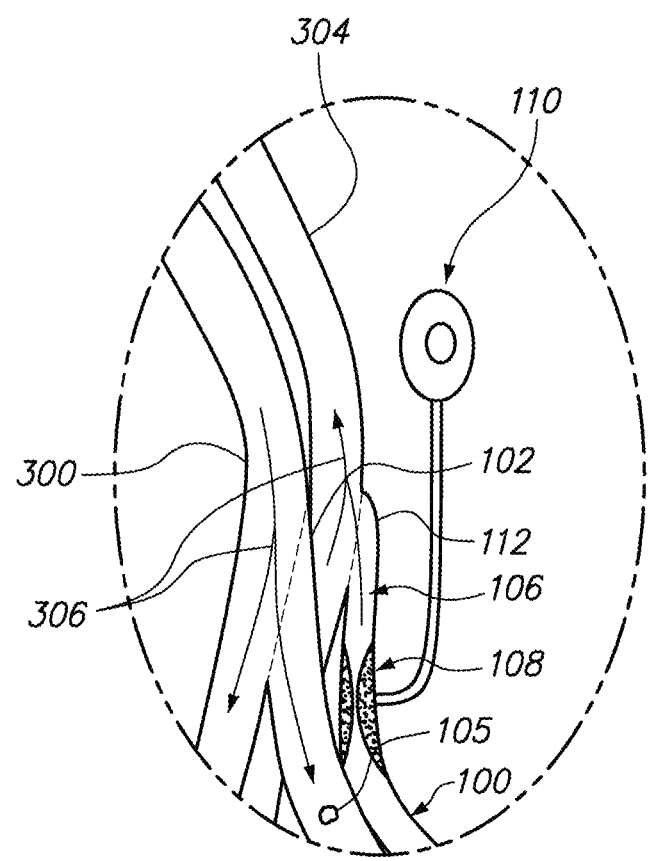
FIG. 3B is an enlarged detail view of the proximal connections of the vascular bypass graft of FIG. 1.

Reference is now made to FIGS. 3A and 3B which illustrate an embodiment of the vascular bypass graft 100 attached to a patient's vascular system. The proximate vascular bypass end 102 of the vascular bypass graft 100 is attached to a patient's artery 300 at a proximate end located upstream from the vascular occlusion 302. This results in blood flow 306 being diverted into the vascular bypass graft 100 from the artery 300. The proximate venous end 112 is attached to a patient's blood vessel 304 of lower pressure, to permit blood flowing through the venous outflow limb 106 to return to the patient's vascular system.

Figure 4A:
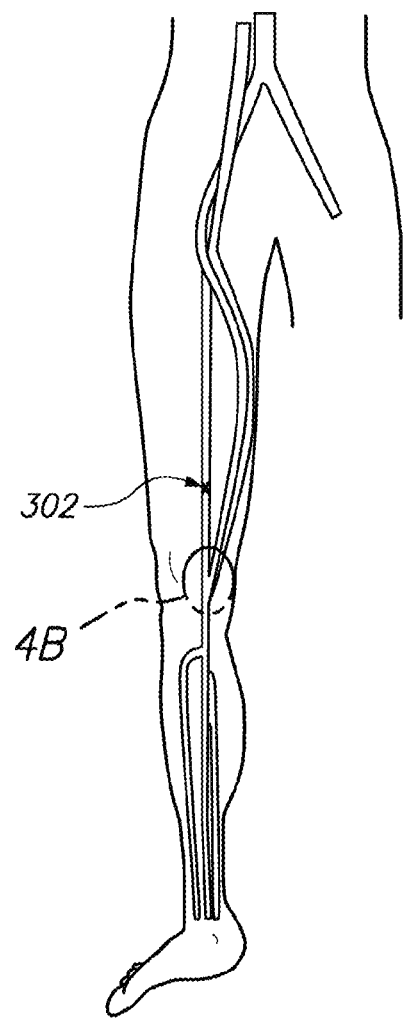
FIG. 4A is a regional view of the distal connections of the vascular bypass graft of FIG. 1.
Figure 4B:
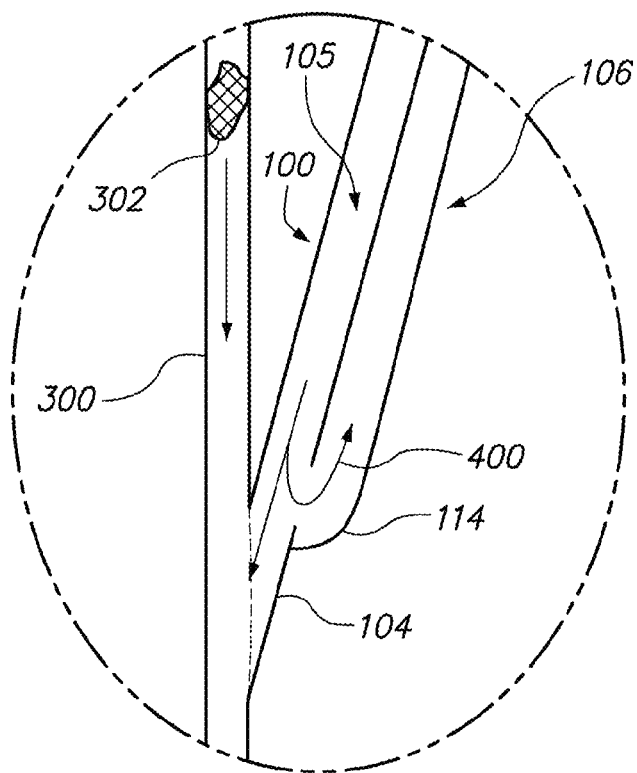
FIG. 4B is an enlarged detail view of the distal connections of the vascular bypass graft of FIG. 1.

FIGS. 4A and 4B illustrate the distal end of the vascular bypass graft 100 attaching to a patient's vascular system. The distal vascular bypass end 104 of the vascular bypass graft 100 is attached to a patient's artery 300 at a distal end located downstream from the vascular occlusion 302. The blood flow that was diverted into the vascular bypass graft 100 from the artery 300 as described above reenters the artery at a location beyond the vascular occlusion thus bypassing the vascular occlusion 302. As seen in FIG. 4B, a portion of the blood flow 400 through the vascular bypass graft's 100 primary graft 105 is diverted into the venous outflow limb 106 through the distal venous end 114 for subsequent return into the patient's vascular system by way of blood vessel 304 as shown in FIG. 3B.

It should be noted that the vascular bypass graft 100 as shown in FIGS. 3A, 3B, 4A, and 4B is shown in a particular vascular configuration. However, the vascular bypass graft 100 is designed to be utilized in any other suitable vascular system including but not limited to the upper extremity, the coronary arterial system and the abdominal, or pelvic vascular system.

Figure 5A:
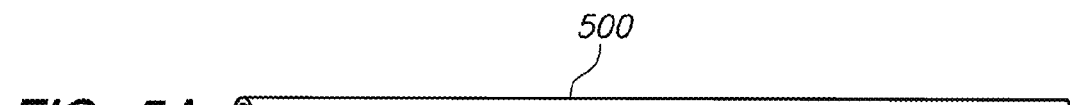
FIGS. 5A, 5B, 5C, 5D and 5E illustrate a series of alternate embodiments of an vascular bypass graft.
Figure 5B:
Figure 5C:
Figure 5D:
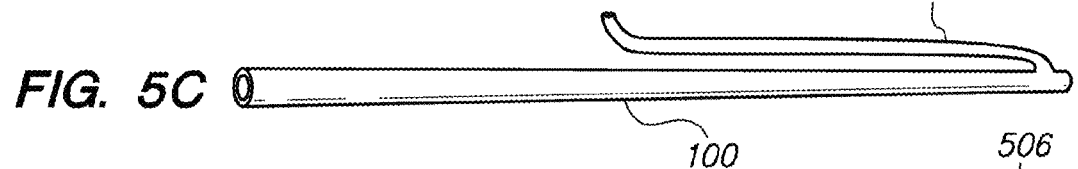
Figure 5E:
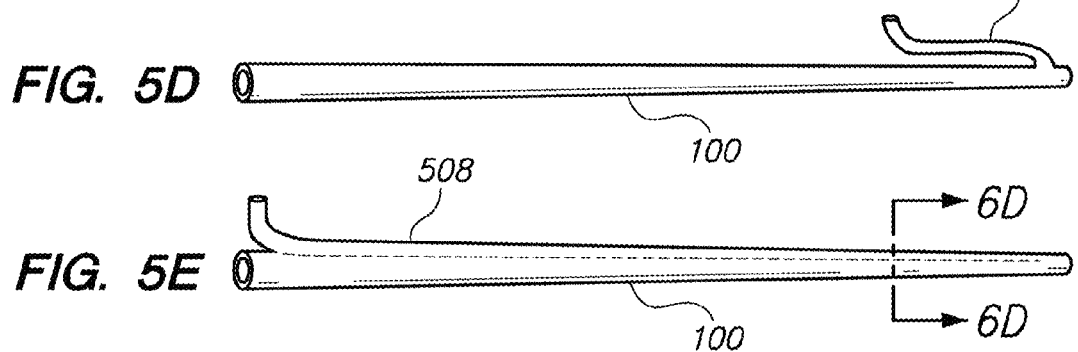
Figure 6A:
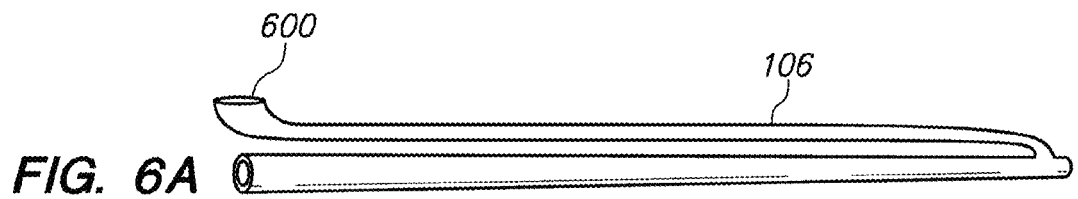
FIG. 6A illustrates an alternate embodiment of a vascular bypass graft having a flared venous outflow limb.

Several variations of the vascular bypass graft 100 are shown in FIGS. 5B through 5E in comparison to a known standard bypass graft 500 as shown in FIG. 5A. The design of the venous outflow limb may take on various configurations including the side-by-side configuration shown in FIGS. 5B through 5D and cross-section FIG. 6B. In another embodiment, the vascular bypass graft 100 has a unitary construction with the venous outflow limb 106 being integrally formed with the vascular bypass graft 100 as shown in FIGS. 5E, 6A, and cross-section FIG. 6D. In the embodiment shown in FIG. 5B, the vascular bypass graft 100 comprises a long venous outflow limb 502. In another embodiment, the venous outflow limb may be a medium length venous outflow limb 504 as shown in FIG. 5C. In yet another embodiment, a short length venous outflow limb 506 may be configured with the vascular bypass graft 100 as shown in FIG. 5D.

It is contemplated that the various lengths of the venous outflow limbs are selected and implemented as required by the medical circumstances. For example, in one patient, the distal vascular bypass end may be located very close to a patient's vein and a short venous outflow limb 506 would facilitate connection of the venous outflow limb to the native vein in the most efficient manner. In contrast, the distal vascular bypass end may be located far away from a patient's native vein and the use of a long venous outflow limb 502 would be necessary. It is further contemplated that there are many variations with respect to the length of the venous outflow limb and other configurations are possible within the scope of the invention disclosed herein.

In one embodiment, the vascular bypass graft, including its primary graft portion and its venous outflow limb portion, are adjustable, separately or as a whole, such as by a cut-to-length fit during surgery to specially fit the vascular bypass graft to a particular patient.

FIG. 5E shows the embodiment where a venous outflow limb 508 is integrally formed with the vascular bypass graft 100. This integral venous outflow limb 508 makes the vascular bypass graft 100 easier to surgically place because there is primarily only one member to manipulate during the installation of the graft. By combining this venous outflow limb 508 with the primary structure of the vascular bypass graft 100 tangling or damage to this venous outflow limb 508 during surgery is reduced. As with the other embodiments, this venous outflow limb 508 can be made any length, independent of the length of the vascular bypass graft 100. The length of this venous outflow limb 508 also being dependant upon the distance required to extend to the best outflow attachment blood vessel.

Figure 6C:
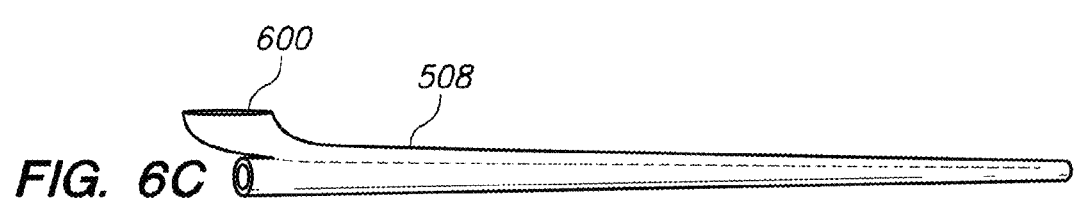
FIG. 6C illustrates an alternate embodiment of a vascular bypass graft having an integral flared venous outflow limb.
Figure 6B:
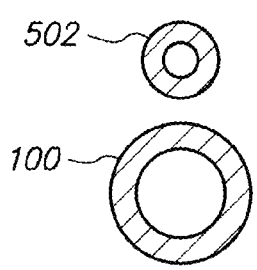
FIG. 6B is a cross-sectional view of the alternate embodiment of FIG. 6A.
Figure 6D:
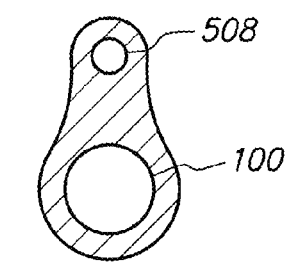
FIG. 6D is a cross-sectional view of the alternate embodiment of FIG. 6C.

In another embodiment, shown in FIGS. 6A and 6C, the venous outflow limb is configured with a flared proximate venous end 600. The flared proximate venous end 600 functions as a fluid diffuser that reduces the exit pressure of blood leaving the proximate venous end prior to re-entry into the patient's vascular system. As a result, the blood flow entering the patient's blood vessel is at a substantially similar pressure which reduces chances of blood clotting, and potential damage to the vascular walls at the re-entry blood vessel. A high pressure differential at the proximate venous end could result in repeated expansion and contraction of the re-entry blood vessel which in turn leads to scarring and thus narrowing of such blood vessel.

Additional embodiments may provide various means for adjusting or controlling the restrictor controller and/or the stenosis restrictor, including various pumps, valves, and devices for adjusting the stenosis restrictor or any other device, which may be dependant on the type of restrictor used. If a balloon-type stenosis restrictor is used, then a deflating/inflating device may be used to control the restriction on blood flow.

Figure 7A:
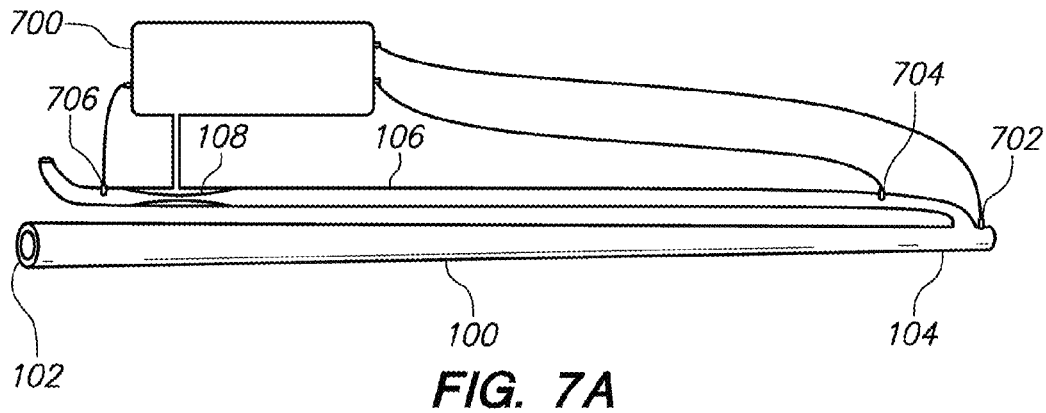
FIG. 7A illustrates an alternate embodiment of a vascular bypass graft having a controller.

In the embodiment shown in FIG. 7A, a controller 700, which may be electrical, mechanical, or a combination of both, is utilized to control the stenosis restrictor 108. The controller 700 can operate in conjunction with various combinations of graft output sensors 702, venous limb high pressure/flow sensors 704, or venous limb low pressure/flow sensors 706.

These sensors monitor one or more fluid dynamic parameters within the vascular bypass graft and provide this information to the controller 700 via electrical, optical, mechanical or other signaling. Fluid dynamic parameters are data relating to the movement of fluid within the vascular bypass graft such as but not limited to blood flow rate, pressure, or both. Fluid dynamic parameters may also include characteristics of the vascular bypass graft itself such as but not limited to the length and volumetric capacity of various sections of the vascular bypass graft.

Data comprising fluid dynamic parameters may be collected from the sensors in a variety of ways. In one embodiment, some or all the sensors are activated by the controller 700 when the controller requires or requests sensor information. However, in other embodiments, the sensors may continuously provide sensor information which the controller 700 may periodically, continuously, or at any other time collect. The controller may be operatively coupled to the stenosis. The term operatively coupled is defined to mean connected to or in communication with, such as by mechanical, physical electrical, pneumatic, magnetic, radio, or any other means.

Figure 7B:
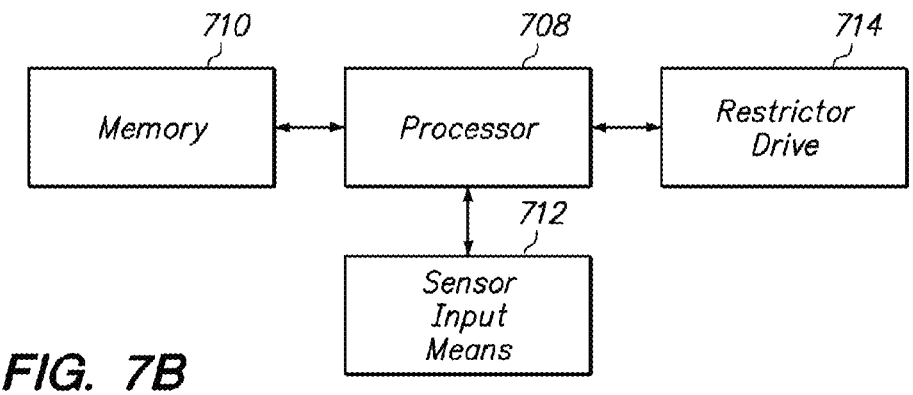
FIG. 7B is a block diagram of an exemplary embodiment for a closed-loop feedback controller of FIG. 7A.

FIG. 7B illustrates internal components for one embodiment of the controller 700. In this embodiment, the controller 700 has a processor 708 with memory 710 for storing machine executable code and sensor information. The machine executable code includes one or more sets of instructions which are interpreted or executed by the processor 708 to accomplish a desired result. In one or more embodiments, the machine executable code may instruct the processor 708 to collect sensor information, perform calculations upon or process the sensor information, and provide an output. This output may be used to control a restrictor driver 714 which controls the stenosis restrictor. The processor 708 may execute or the machine executable code may instruct the processor to use the memory 710 to store and/or retrieve data including but not limited to sensor information, intermediate or final outputs, or additional machine executable code. Communication between the internal components of the controller 700 may be bi-directional.

In one or more embodiments, the processor 708 may base its output or commands to the restrictor driver 714 on a plurality of sensor information collected through sensors connected to a sensor input 712. The controller 700 may be programmed to manually, periodically, or continuously monitor and adjust the performance of the vascular bypass graft based on fluid dynamic parameters such as but not limited to pressure or flow rate or both collected from various sources and sensors. The processor 708 may then adjust the stenosis restrictor accordingly.

For example, the vascular bypass graft 100 illustrated in FIG. 7A may be fitted with one or more of a graft output sensor 702, a venous limb high pressure/flow sensor 704 and/or a venous limb low pressure/flow sensor 706. The information from these sensors is communicated to the controller 700 to form a closed-loop feedback control system for dynamic adjustment stenosis, which in turn controls the flow through the outflow limb, which in turn controls the flow through the vascular bypass graft 100. It is contemplated that the invention may be practiced with additional or fewer sensors 706 depending on the degree of flow control needed for a particular application.

Figure 7C:
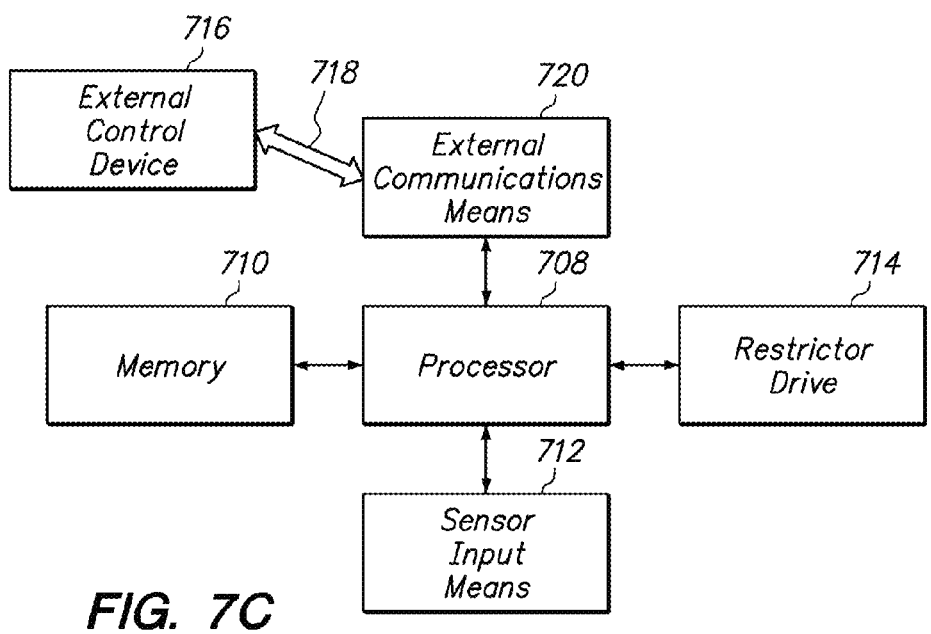
FIG. 7C is a block diagram of an exemplary embodiment for an open-loop feedback controller of FIG. 7A.

In another embodiment shown in FIG. 7C, the controller 700 is configured as an open-loop control system. In this variation, the processor 708 may communicate with an external control device 716. In this embodiment, the processor 708 may receive information from its sensor input 712 and then send the information to an external communication device 720 which transmits this information to an external control device 716. The processor 708 may also process the information prior to sending it to the external communication device 720.

In one embodiment, the external control device 716 may have a similar internal makeup as the controller 700. For example, the external control device 716 may comprise a processor, memory, external communication device, and sensor input. Thus, the external control device 716 may receive information from sensors, other devices, or other sources. When operating, the external control device 716 may perform some or all of the processing ordinarily done by the controller's 700 processor 708 or may supplement the processed output of the processor 708 through bi-directional communication with the processor 708. In addition, the external control device 716 may perform diagnostics on the controller 700, or record and/or relay information it receives to medical personnel for treatment purposes. In one or more embodiments the external control device 716 may be a computer.

The transmission of information can be a bi-directional communication link 718 with the external control device 716 such as by way of wireless connection such as radio transmission, microwave radio transmission (telemetry), and radio frequency identification methods. Alternately, the bi-directional communication link 718 may be effectuated by a direct connection with the external control device 716 such as by an externally accessible electro-mechanical connector.

Once the information is received by the external control device 716, the information may be evaluated and data may be transmitted back to the processor 708 via the bi-directional communication link 718. In one embodiment, the data causes processor 708 to signal the restrictor driver 714 to adjust the stenosis restrictor as necessary to achieve the desired flow rate and pressure. However, the processor 708 may further process the data prior to signaling the restrictor driver 714.

The above embodiment provides a bypass graft flow control system that may continuously or periodically monitor and adjust the flow rate through the vascular bypass graft and venous outflow limb in real-time. In this embodiment, the controller monitors the flow rates in the graft and adjusts the magnitude of the stenosis restrictor to thereby maintain or modulate the flow rate which in turn will reduce clotting.

It is also contemplated that the flow through the vascular bypass graft may be controlled in a time-variant manner. The controller may be configured to selectively open and close, to any degree, the stenosis restrictor at predetermined time intervals to purge or clear the vascular bypass graft of lingering low velocity blood flow thereby reducing or inhibiting blood clots. Additionally, alternative embodiments may purge or clear the vascular bypass graft whenever a sufficiently low velocity blood flow is detected.

It is contemplated that another variation of the vascular bypass graft disclosed herein is configured with a fixed stenosis restriction. In this variation, the blood flow restriction in the venous outflow limb is non-adjustable. Thus, the proper flow rate through the vascular bypass graft would be determined and configured during its manufacture or when placed in a patient. Multiple different vascular bypass grafts of differing fixed flow rates can produced with the vascular bypass graft of proper fixed flow rate selected for a particular patient prior to surgical placement. This embodiment reduces manufacturing complexity and cost while maintaining the vascular bypass graft's resistance to occlusion by clotting.

In one or more embodiments, the vascular bypass graft 100 may be formed with a vascular connector 804, such as shown in FIGS. 8A-8D. In this manner, rather than having a venous outflow limb 106 and primary graft 105 various lumen may be attached to the vascular connector 804 to form such structures. For example, a patient's native veins could be attached to the vascular connector 804 to form a venous outflow limb 106, a primary graft 105, or both. The advantages as described above would also be present in these embodiments of the vascular bypass graft. The vascular connector 804 is beneficial in that it allows more of the vascular bypass graft 100 to be formed from a native veins, which generally have improved patency as compared to synthetic lumen. Other natural lumen could be used with the vascular connector 804 as well. For example, a vein grown in a laboratory could be used to form the primary graft 105, venous outflow limb 106 or both.

Figure 8A:
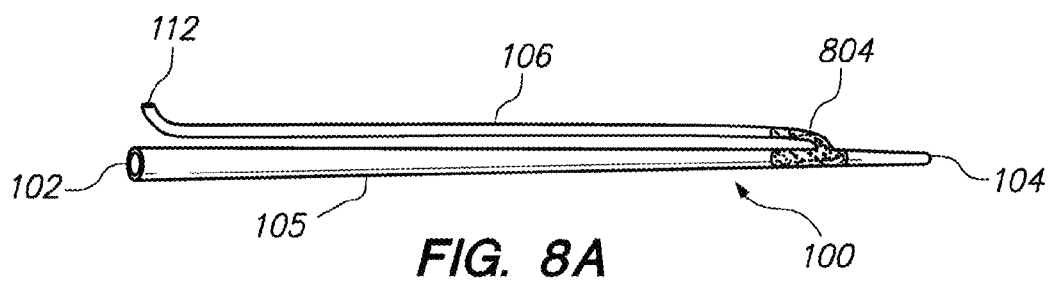
FIGS. 8A, 8B, 8C and 8D illustrate a series of alternate embodiments of a vascular connector.

FIGS. 8A-8D show various configurations of a vascular connector 804. In FIG. 8A, the vascular connector 804 is configured as a branch point from which the venous outflow limb 106 may extend from the primary graft 105. This configuration provides the benefit of providing a connector 804 which may connect to native or synthetic vessels, collectively 106, 105, 104 as determined by the treating physician and the condition of the patient.

Figure 8B:
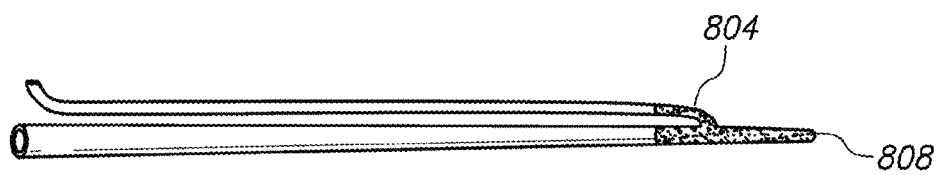

FIG. 8B illustrates an embodiment having an elongated vascular bypass end 104. In this embodiment, the vascular connector 804 has an elongated portion 808 at the vascular bypass end 104 for connecting to the vascular system. One benefit to this configuration is that the elongated portion 808 is part of the connector 804 which decreases the time required to attach the connector to the patient.

Figure 8C:
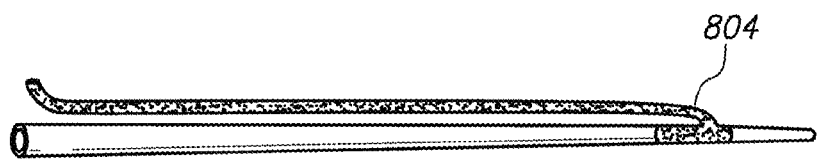
Figure 8D:

FIG. 8C illustrates an embodiment where the venous outflow limb 106 is part of the vascular connector 804. In such an embodiment, a native vessel may be used for the primary graft 105. This provides the benefit of allowing greater use of the patient's native vessel, which reduces the chance of clotting. FIG. 8D illustrates an embodiment similar to FIG. 8C having an elongated portion 808 which creates an elongated vascular bypass end 104.

Figure 9A:
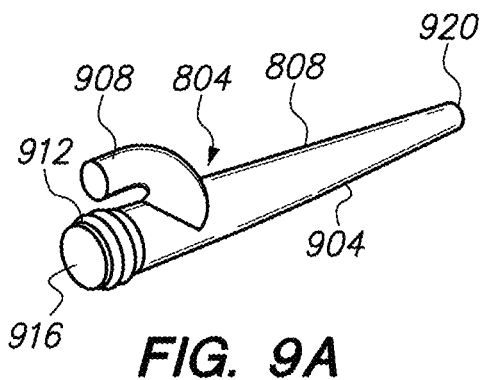
FIGS. 9A, 9B, and 9C illustrate exemplary embodiments of a vascular connector.
Figure 9B:
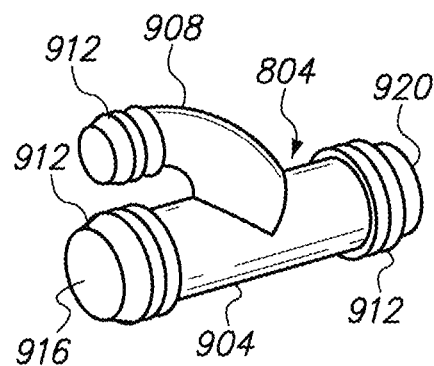
Figure 9C:
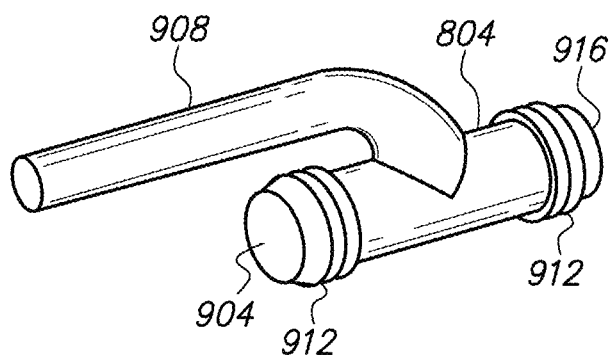

Further details regarding the vascular connector will now be disclosed with regard to FIGS. 9A-9C. As can be seen, the vascular connector 804 may comprise a venous outflow stem 908 and a primary graft stem 904. The venous outflow stem 908 may extend from the primary graft stem 904. For example, the venous outflow stem 908 may extend from an opening in the side or a wall of the primary graft stem 904. An outflow end of the venous outflow stem 908 remote from the primary graft stem 904, may connect to the vascular connector 804 to a venous outflow limb, which may be a native vessel, synthetic lumen, animal lumen, grown lumen, or other lumen. Referring to FIG. 9C, it can be seen that the venous outflow stem 908 may have an elongated shape, such as to form part of or all of a venous outflow limb. It is noted that the venous outflow stem 908 may be a separate tubular structure attached to the primary stem 904, or may be integrally formed as an extension from the tubular structure of the primary stem.

The primary graft stem 904 may be used to connect a primary graft (105, FIG. 8A) to the vascular connector 804. For example, a vein or other natural or synthetic lumen could be connected to the vascular connector such as at end 916 or 920 via the primary graft stem 904. Typically, the primary graft stem 904 will have a larger diameter than the venous outflow stem 908 so as to produce the blood flow dynamics described above. Namely, to direct blood flow primarily through the primary graft stem 904 while diverting a portion of the blood flow through the venous outflow stem 908. This ensures an adequate blood flow through the vascular connector to prevent clots and improve the patency of the vascular connector. As can be seen from FIG. 9A, the primary graft stem 904 may be tapered to adjust the blood flow though the vascular connector 804. For example, to reduce the blood flow out of the vascular connector 804 an outflow end 920 of the vascular connector may be formed with a reduced diameter.

The primary graft stem 904 may have a first end and a second end through which blood may flow. For example, as shown, the vascular connector 804 has a first vascular bypass end 916 and a second vascular bypass end 920. In general, the primary graft stem 904 will form at least part of a conduit or lumen which is used to bypass a blockage in the vascular system. To illustrate, in one embodiment, the first vascular bypass end 916 may be connected upstream of a clot or other blockage while the second vascular bypass end 920 may be connected downstream of the blockage (or vice versa). The blockage is thus bypassed in this manner. It is contemplated that one or more natural or synthetic lumen could be connected to the first or second vascular bypass ends 916,920 or both. In one or more embodiments a "bridging" lumen could be used. For example, a synthetic (or other lumen) may be used to bridge a distance between the first or second vascular bypass end 916,920 and the vascular system. The step of connecting may comprise stitching, clamping, or friction fitting or any other means for connecting known in the art or developed in the future.

It is contemplated that the vascular connector 804 may have one or more textured portions or raised portions to facilitate connections with various lumen. For example, as shown, the vascular connector 804 comprises a set of angled ridges 912 configured to allow the ends of the vascular connector to enter a lumen and to hold the vascular connector in position once inserted. For instance, the angle of the ridges 912 aids in insertion of the vascular connector 804 but resists or restricts removal of the vascular connector. This helps secure the vascular connector 804 to a lumen. As can be seen, the ridges 912 may be at one or more ends of the vascular connector 804. FIG. 9A shows the ridges 912 only at one end 916 of the primary graft stem 904 for example. FIG. 9B shows ridges 912 at each end 916,920 of the primary graft stem 904 as well as at the end of the vascular outflow stem 908, while FIG. 9C shows ridges 912 only at the ends 916,920 of the primary graft stem 904.

The vascular connector 804 may be implanted in various ways. In general, the venous outflow stem 908 will be connected to a vessel of lower pressure. Such connection may be made through one or more lumen connected to the venous outflow stem 908. The primary graft stem 904 may be connected in a similar fashion. Namely, the first and second ends 916,920 of the primary graft stem 904 may be connected to a vein or artery directly or through one or more lumen. As stated, one end of the primary graft stem 904 will typically be upstream from a blockage while the other is downstream from the blockage so as to bypass the blockage. In one or more embodiments, the ends 916, 920 of the primary graft stem 904 may be connected to an artery while the venous outflow stem 908 is connected to a vein, such as described above.

The vascular connector 804 is also beneficial in that it may be a relatively compact size and thus potentially more easily implantable in patients. In addition, the compact size allows the vascular connector 804 to be formed from rigid material if desired. The rigid material may be more durable and may be more consistent in providing a desired pressure since it is less likely to deform than a non-rigid material.

It is also contemplated the interior of the vascular connector or connecting native or synthetic vessels, collectively 106, 105, 104 may be lined with a substance or coating that resists clotting or rejection. For example, Allograft is a graft of tissue obtained from a donor of the same species as, but with a different genetic make-up from, the recipient, as a tissue transplant between two humans. This may also be called homograft. Xenograft is a graft in which the donor and recipient are of different species. An example is a vein harvested from a pig, or other animal, then used in a human. Bioengineered tissues is tissue that is grown in the lab using cells from humans or animals that can be used to create organs, skin and vessels. Drug eluting materials and chemicals may be embedded into a medical device that slowly releases a drug to block cell proliferation. This prevents fibrosis that, together with clots (thrombus), could otherwise block the artery, a process called restenosis The primary reason for the formation of blood clots in a bypass graft is that the blood flow through the graft is of such low velocity that blood clotting mechanisms are triggered. Regions of low velocity blood flow are common in the body's smaller vessels such as veins and capillaries. Low velocity regions are also found in the transitions between larger vessels, such as arteries, to smaller ones, such as veins or capillaries because the reduction in size reduces flow capacity and thus blood flow velocity is also reduced. Therefore, if a bypass graft is attached to a small vessel at its outflow end or in a region of low velocity blood flow, only a small amount of blood at low velocity flows through the graft creating circumstances where blood clots may likely form within the graft. This will cause occlusion of the graft and eventual graft failure.

An additional advantage that the design provides is increased flow allowing energy dissipation of each pulse wave that otherwise is absorbed into the distal anastomosis at the graft and native artery interface. It is asserted that this added energy transmitted with current graft design causes an inflammatory response which leads to early stenosis development and hence early graft failure. Increasing the flow through the graft lessens this water-hammer (blood-hammer) effect helping to maintain graft patency.

In general, a vascular bypass graft which improves blood flow in occluded vascular regions and which is resistant to occlusion by blood clots is disclosed. The method of creating a vascular bypass graft disclosed herein has several advantages over known bypass grafts. One such advantage is that this method creates a graft which maintains a high blood flow velocity in conditions where there would otherwise be a low flow rate through the graft, such as where outflow from the distal vascular bypass graft end is low or reduced. In addition, creation of the graft may be made with available vessel members without the need for complex, risky, or time consuming method. Currently known grafts will not stay un-occluded in low flow rate conditions because the slow flow through the graft allows blood clots to develop and occlude the graft eventually rendering it non-functional. Several embodiments of the graft have been described below and this application claims priority to and incorporates by reference all of the subject matter in the following patent applications:

| | | |
|---|---|---|
| Vascular Connector - Bypass Graft Improvement Design | 13/212,129 | Filed: Aug. 17, 2011 |
| Bypass Vascular Graft | 11/977,953 | Filed: Dec. 07, 2006 |

The grafts disclosed herein may be created from single and/or multiple components utilizing a variety of materials. Disclosed herein is an alternative method which employs a variety of materials and methods to create the basic component of the unique bypass graft configuration combined during the bypass procedure or preformed prior to graft placement. The method disclosed is a method graft creation from any one or more materials including but not limited to a person's own vein (autologous vein), human umbilical vein (HUV), Graft Donor (homologous grafts), Bioengineered graft and synthetic materials such as polytetrafluoroethylene (PTFE) or Dacron, alone or with the blood thinning agent such as heparin bonded to the inside of the graft.

Figure 10:
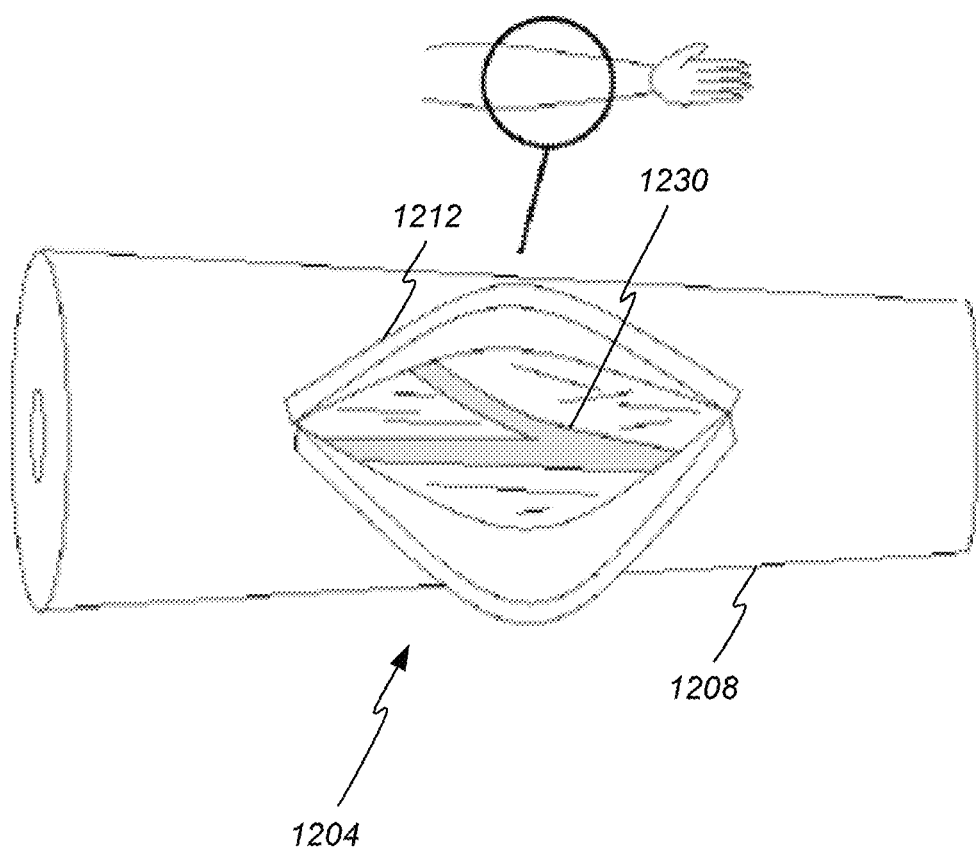
FIG. 10 illustrates an example of a vessel harvest site shown as the forearm with a Y-shaped vessel exposed (A1).

Referring now to the drawings, FIG. 10 illustrates an example of a graft harvest location 1204 or the forearm 1208 as shown. The magnified forearm referenced figure is shown with an operative incision 1212 that is made to thereby demonstrate and show tissues below the skin, in particular the y-shaped vessel 1230. The incision can be made using any known technique including scapel or other cutting tool, laser knife or "Bovie" type electrosurgical cutting tool. One or more incisions are made to expose the vessel 1230, which may be a vein or artery.

Figure 11:
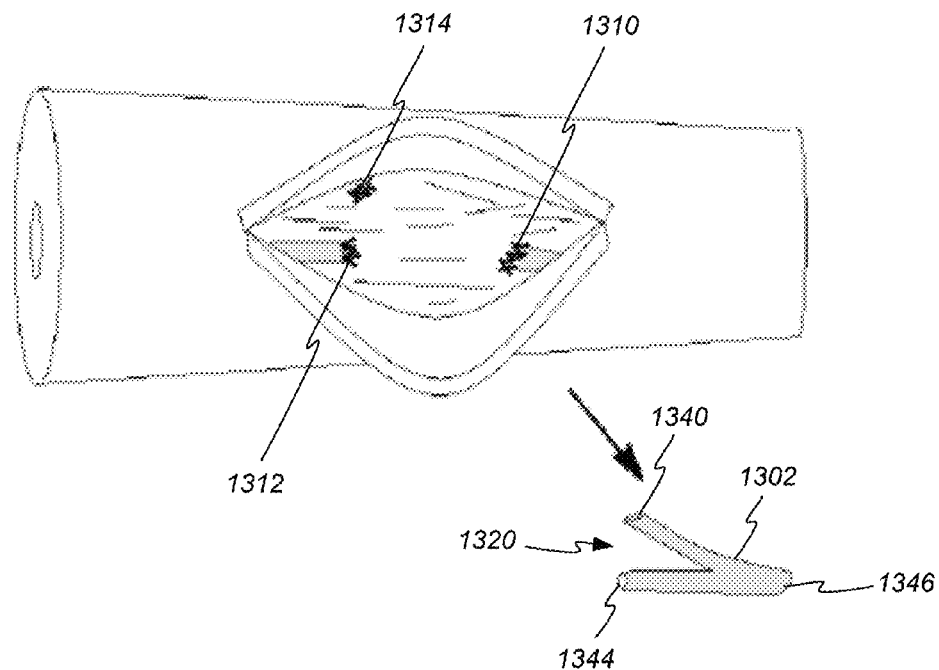
FIG. 11 illustrates a harvested Y-shaped vessel segment (2B) with sutures placed on remaining vessel segments (2A).

Branching arteries and veins are seen commonly throughout the body. In the first method of bypass creation, a branching segment becomes the foundation for the bypass graft. This segment is dissected out of the forearm as shown in FIG. 11. As shown, to remove the segment of the vessel which is missing in FIG. 11 by making an incision (or ligating, or stipping) of the vessel at incision sections 1310, 1312, 1314 to remove section 1302. The removed section 1302 has a branch 1320. The drawings are not to scale or limited to the particular scale or relational size of each element. The diameter or size of teach segment or branch may be selected to formed to suit the patent needs.

Thereafter, the remaining sections at the incision sections 1310, 1312, 1314 are sewn or sutured closed 200. Any method may be used to close the ends of the vessels 1310, 1312, 1314 including clamps, clips, ties, heat closure techniques, stitches, or any other method or system. It is also contemplated that other vessels (organic or manufactured) may be connected to the ends 1310, 1312, 1314 to establish blood flow. Hence, blood conducting passages material may be surgically implanted to replace the removed section. Because this location is not a location that is not at high risk of clotting artificial or organic vessels may be used such as other vessels or grafts.

In this embodiment the harvest branched section is defined by a first end 1346, a second end 1344 and a third end 1340. An opening capable of accepting blood flow into the harvested section 1302 is associated with each end.

It is contemplated that the harvested segment 1302 could be harvested from a human, such as the patient or a tissue matched donor, or from a cadaver. The harvested segment 1302 could also be from a non-human such as an animal, for example, but not limited to a Bovine graft. In addition, the segment could be grown in a laboratory environment such as from companies cytograft or humanocyte. Or the harvested segment may be manufactured such as out of PTFE, Dacron, plastic, nylon or other material as shown in any of FIG. 9A, 9B, or 9C.

Figure 12:
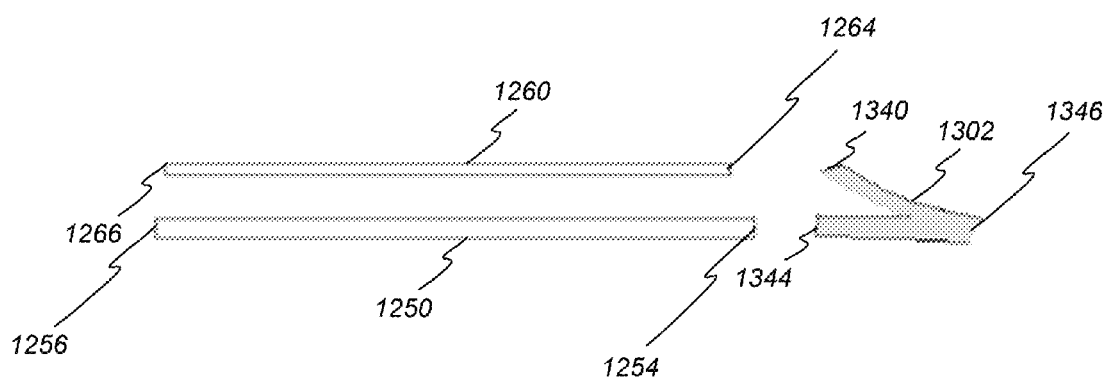
FIG. 12 illustrates a harvested vessel segment (3A) with vessel segments (native, cadaver, bioengineered polymer, animal or other) (3B).

Referring now to FIG. 12, additional segments 1250, 1260 possibly made from any of a multitude of materials (native vein, cadaver, bioengineered materials, polymers and any other described herein) are then used to create the bypass graft in the form of a blood flow passage when connected to the harvested vessel 1302 the end segments are sewn together. The segments 1250, 1260 may be of any length and may be cut or trimmed to a certain length to establish graft lengths for connection as described herein. In this example embodiment, the graft segment 1250 is the primary graft and it has a first end 1254 that connects to the end 1344 of the harvested segment 1302 and a second end 1256 that is distal the first end 1254. In this example embodiment, the graft segment 1260 is the venous outflow limb graft and it has a first end 1264 that connects to the end 1340 of the harvested segment 1302 and a second end 1266 that is distal the first end 1264.

Figure 13:
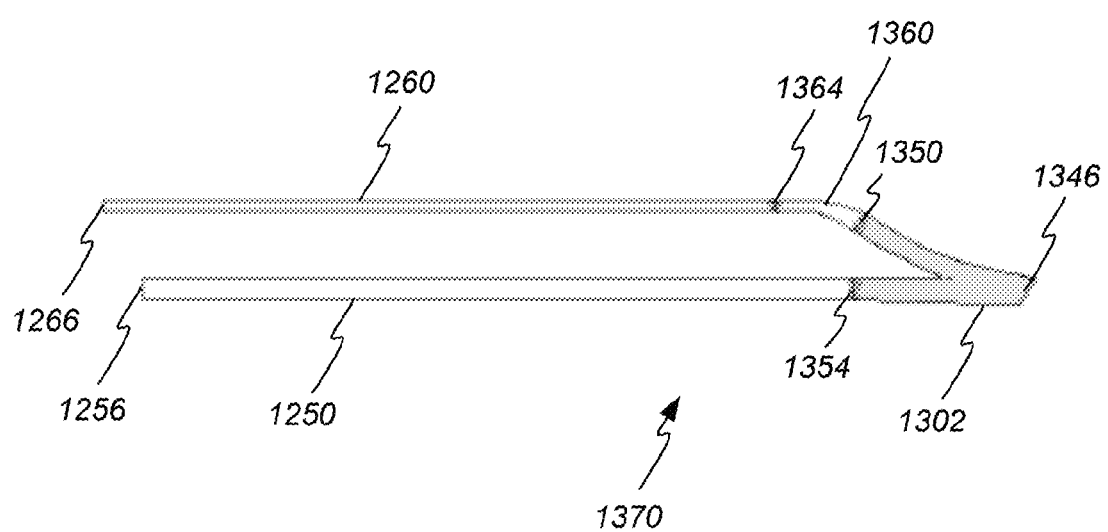
FIG. 13 illustrates an attached harvested or created vessel segment to extension segments.

As shown in FIG. 13, this method creates a composite graft 1370 as shown. The composite graft 1370 is formed by stitching or otherwise connecting the harvested segment 1302 to the primary graft segment 1250 and the venous outflow limb section 1260. To establish this arrangement of vessels, surgical glues, sealants, adhesives, sutures, stitches are made by a surgeon or machine at a suture area 1354 and suture area 1350.

In one or more embodiments, a connector segment 1360 maybe be surgically connected between the harvested segment 1302 and the venous outflow limb section 1260 by stitching or suturing it into place through additional suture 1364. The resulting structure is generally similar to the configuration of FIG. 5A-5E following the method of construction described herein.

Sutures and/or stitching is generally understood by one of ordinary skill in the art, but would be done by a doctor, physician assistant, operation room nurse, operating room technician, medical technician, or lab worker either by hand or using a machine. It is contemplated that method or devices other than traditional sutures may be used to connect the sections 1260, 1250 to the harvested section 1302. For example connectors, having a solid outer section and a hollow inner passage may be provided which connect to each end to thereby facilitate connection. It is also contemplated that Surgical adhesives or sealants could be used to facilitate the connection.

Figure 14:
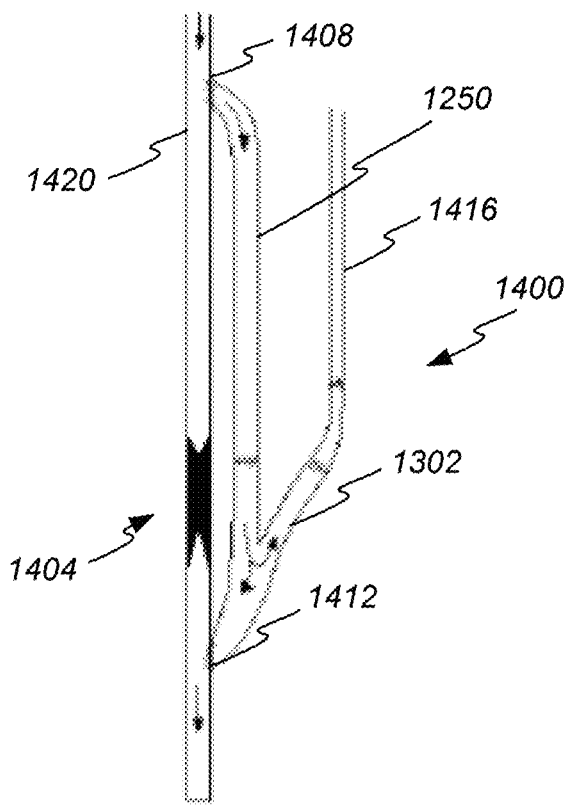
FIG. 14 illustrates a newly created bypass graft attached to diseased native vessel with proximal anastomosis and distal anastomosis (5C) shown in relation to shows the return lim).

As shown in FIG. 14, this composite graft 1400 is then sewn onto the body to thereby bypass the diseased vascular segment 1404 (which is restricted or blocked) of a vessel 1420 with the proximal anastomosis 1408, the sewn distal anastomosis 1412 and the yet unsewn outflow limb 1416.

To achieve this configuration, a surgeon or other medical personnel would incise, such as by cutting, slicing, or clipping, into an existing vessel 1420 at a location 1408 that is upstream of the restricted area 1404. At the location 1408, the surgeon would attach the end of the primary graft segment 1250. The opposing end of the primary graft segment 1250 is attached to the branched section 1302. The end 1346 of the branched segment 1302 also attaches to the vessel 1420, but downstream from the connection location 1408 and downstream from the restriction 1404. The surgeon or other medical personnel would incise, such as by cutting, slicing, or clipping, into an existing vessel 1420 at location 1412. The outflow limb 1416 is shown as being unconnected. The outflow limb 1416 is next connected to a vein (now shown in FIG. 14) such as by forming an incision in the vein and attaching the distal end of the outflow limb 1416 to the vein. This establishes a return path for blood flow cutting from the vessel 1420 to a separate vein such that blood is continually flowing through the outflow limb 1416 and thus always flowing through the primary graft section 1250, which minimizes clotting in both the primary segment 1250 and the outflow limb 1416.

Figure 15:
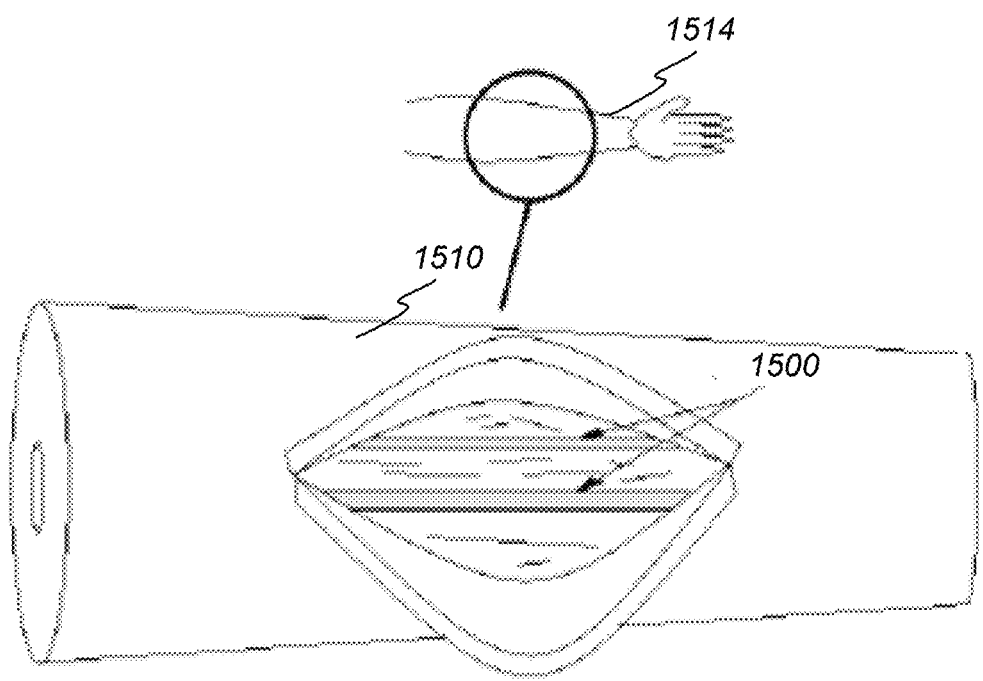
FIG. 15 illustrates two, non-connecting exposed vessels.

An alternative method of creating the Batiste bypass configuration uses straight segments of vessel 1500 as shown in FIG. 15. To access the vessels 1500 a surgeon may form an incision in the tissue 1510 which covers the one or more vessels 1500. The vessels may be taken from any location in the body, such as the arm 1514 as shown, or any other limb or location. It is contemplated that the vessels described herein may be synthetic, such as made from bioengineered materials, PTFE or Dacron and well as these materials coated with heparin, or harvested from an animal donor, a human cadaver or a human donor.

Figure 16:
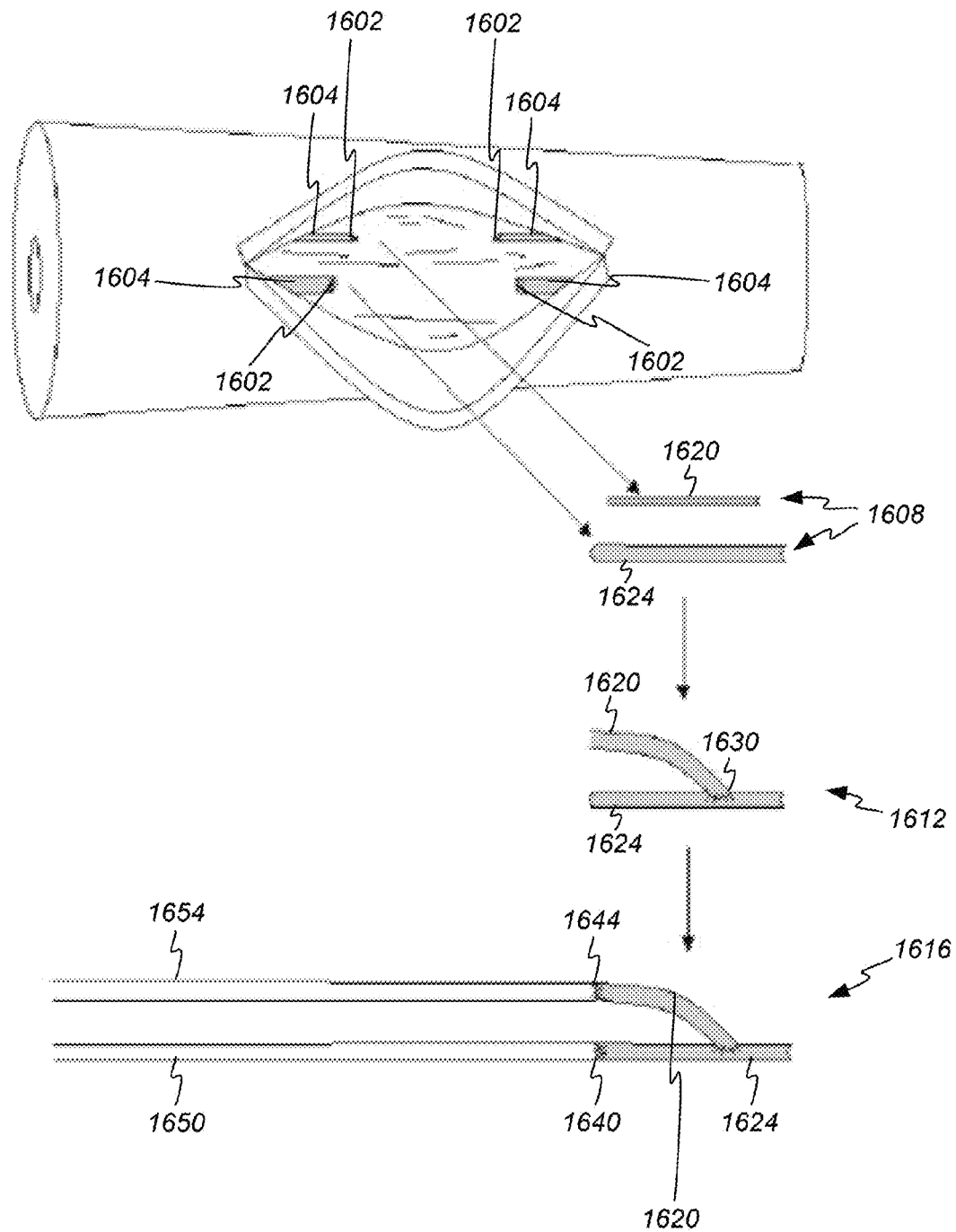
FIG. 16 illustrates sequential construction of the bypass graft from separate individual sections of vessel, or individual materials such as polymer, cryoveins, cadavers, bioengineered, animals or other.

These vessel segments 1608 are shown in FIG. 16 are harvested and the end of the vessels within the harvest site are sewn closed. Removal of these one or more vessels occurs by incising or otherwise cutting the vessel at locations 1602. Ends of the remaining vessels 1604 or sutured or stitched shut, or otherwise closed to prevent blood flow out of the vessel. The remaining vessels 1604 may also be connected using any other type vessel connector, organic or synthetic, (not shown) to reestablish blood flow or remain closed with other collateral pathways compensation for the removed vascular segments.

The removed straight segments 1608 are then combined into a Y-shaped configuration 1612 as shown or in any other shape or Y-shaped configuration, such as a branched configuration. The segments 1608 may be selected to be sized such that one of the segments 1608 is a venous outflow limb 1602 while the other segment is a primary bypass 1624.

Formation of the y-shaped configuration 1612 occurs by the surgeon optionally forming an end of the bypass limb 1620, such as by cutting or trimming, so that it will connect to a generally straight primary graft 1624. An opening or other access port is formed in the primary graft 1624 to allow fluid flow out of the primary graft. The proximate end 1630 of the bypass graft 1620 is then connected to the opening formed in the primary graft 1624 to establish a fluid flow pathway from the primary graft, through the opening therein, into the bypass graft.

This Y-shaped configuration 1612, disclosed originally the Batiste bypass patent application, is then combined with any type material, such as tubing, straight grafts, organic vessel (human or non-human), or any other material disclosed herein to form the bypass graft 1616. This bypass graft 1616 is then utilized to bypass a diseased vessel segment 1404 as shown in FIG. 14.

To connect the Y shaped (branched) section 1624 to the two other sections 1650, 1654, a surgeon would perform an end to end anastomosis using sutures, clips or surgical adhesives. In other embodiments, a machine, technician, or robotic device may be used to attach, at connection seam 1644, the bypass outflow segment 1654 to the section 1620. A similar connection can be made between primary graft portion 1650 and the section 1624 at seam 1640. Connections or seams 1640, 1644 should be established to provide a fluid path from segment 1620 to segment 1654 and between segment 1650 to segment 1624.

Figure 17:
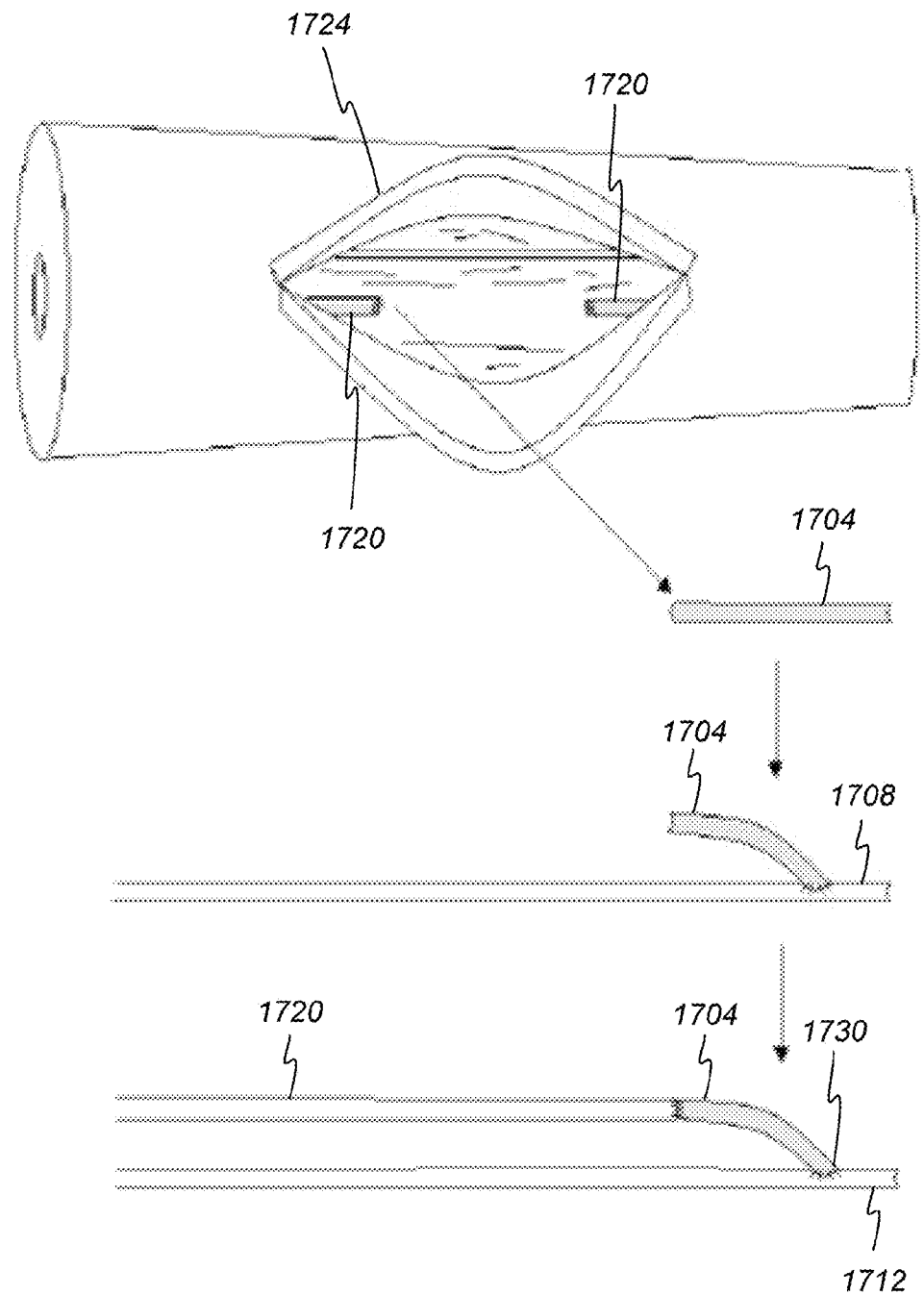
FIG. 17 demonstrates construction of the bypass graft from a single piece of material attached to other numerous possible materials.

As shown in FIG. 17, a third method of creating the Batiste Y-shaped bypass graft is to employ a single section of vessel 1704 (either harvested or synthetic) and attach it to a multitude of materials in the Batiste Y-shaped bypass configuration 1704, 1708. This segment can then be sewn into the patient to bypass the diseased vesicular segment 1420 as shown in FIG. 14. The processes of removing the segment 1704 from the body (living or cadaver, human or non-human) occurs as described above. The process of connecting the proximal end 1730 harvested segment 1704 to the non-harvested bypass graft segment 1720 occurs as described above. The process of connecting the harvested segment 1704 to the non-harvested primary graft segment 1712 occurs as described above. Although shown in a particular configuration in FIG. 17, it is contemplated that any type configuration of native and non-native elements may be combined to establish the graft design shown.

The process of creating any incision, or cutting could use a laser or electrosurgical means and could be performed by a surgeon or other trained medical personnel. It is also contemplated that a machine or robotic device could be utilized to perform any of the steps described herein, such as forming incisions, cuts, sutures, applying clips, using adhesives and vessel attachment.

It is contemplated that the processes and method described herein could be performed prior to or at the time of surgery. In one exemplary process, the bypass grafts described herein could be constructed at a facility or factory and then packaged in a saline solution or other preservative for use by a doctor at a later date, such as the time of surgery. The organic or synthetic vessels may thus be assembled into the configuration described above at a medical lab and at a time not associated with a medical procedure. Testing may also occur at that time to achieve a complete or near fluid tight seal at the one or more segments. Various sizes of grafts (both primary graft segment and bypass graft segment) may be constructed and determined through measurement to allow a hospital or doctor to purchase and use the ideal graft size for the patient This provides the benefit of having the bypass graft made at a lower cost since it can be done by personnel or machines and not doctors. In addition, making the bypass graft at a time prior to the time of surgical implant reduces the time that the patient is under anesthesia and prevents additional surgical procedures upon the patient. Bioengineered graft segments whether form the patients DNA or a donor could be made prior to any surgery. As stated above, more thorough testing can be performed when constructed in a medical lab when the patient is not under anesthesia.

It will be understood that the above described arrangements of apparatus and the method therefrom are merely illustrative of applications of the principles of this invention and many other embodiments and modifications may be made without departing from the spirit and scope of the invention as defined in the claims. Any of the steps may be performed in any order and steps may be eliminated.

What is claimed is:
1. A method for constructing a vascular bypass graft comprising:
providing a first tubular segment having a first tubular segment internal passage having a diameter configured for fluid flow, the first tubular segment having a distal end with a distal end opening and a proximal end with a proximal end opening, the distal end opening and the proximal end opening accessing the first tubular segment internal passage;

providing a second tubular segment having an second tubular segment internal passage configured for fluid flow, the second tubular segment having a distal end with a distal end opening and a proximal end with a proximal end opening, the distal end opening and the proximal end opening accessing the second tubular segment internal passage, and the second tubular segment having a diameter that is less than a diameter of the first tubular segment;

forming an opening completely contained in a side wall of the first tubular segment near but inward from and not touching the proximal end of the first tubular segment;

preparing the distal end and the proximal end of the first tubular segment to be capable of surgical attachment to a first blood vessel;

preparing the distal end of the second tubular segment to be capable of surgical attachment to second blood vessel;

preparing the proximal end of the second tubular segment to be capable of surgical attachment to the first tubular segment; and attaching the proximal end of the second tubular segment to cover the opening in the first tubular segment such that the inner passage of the second tubular segment is aligned with the opening to thereby form a fluid pathway from the first tubular segment to the second tubular segment that is separate from the proximal end opening in the first tubular segment.

2. The method of claim 1, further comprising aligning the second tubular segment generally parallel to the first tubular segment with the distal end of the first tubular segment pointing in the same general direction as the distal end of the second tubular segment.

3. The method of claim 1, wherein the opening formed in the first tubular segment has a diameter that is generally matched to the diameter of the second tubular segment.

4. The method of claim 1, further comprising cutting the proximal end of the second tubular segment at an angle of between zero to 90 degrees to prepare it for connection to the first tubular segment.

5. The method of claim 1, further comprising packaging the vascular bypass graft in a container containing the vascular bypass graft and preservative solution.

6. The method of claim 5, wherein the container containing the vascular bypass graft is also frozen or chilled.

7. The method of claim 1, wherein one or more of the first tubular segment and the second tubular segment are constructed from human or animal donor, bioengineered or derived from polymers.

8. The method of claim 1, wherein all of the method steps occur at a medical lab prior to placement of the vascular bypass graft in a patient.

9. A method for constructing a vascular bypass graft for insertion into a vessel having an full or partial occlusion, the vessel having a first diameter, the method comprising:

obtaining a first tubular segment having an internal passage defining a central axis, the first tubular segment having a diameter configured for fluid flow, the first tubular segment having a distal end and a proximal end, each of which having an opening to the internal passage;

obtaining a second tubular segment having an internal passage configured for fluid flow, the first tubular segment having a distal end and a proximal end, the second tubular segment having a second diameter, the second diameter being less than the first diameter;

establishing an opening in a side wall of the first tubular segment near but inward from the proximal end of the first tubular segment, the opening having a diameter than is generally similar to the second diameter; and attaching the proximal end of the second tubular segment to cover the opening in the first tubular segment such that the inner passage of the second tubular segment is aligned with the opening in the side wall to thereby form a fluid pathway from the first tubular segment to the second tubular segment that is fluidly separate from the opening of the proximal end in the first tubular segment.

10. The method of claim 9, further comprising aligning the second tubular segment generally parallel to the first tubular segment with the distal end of the first tubular segment pointing in the same general direction as the distal end of the second tubular segment and the distal end of the second tubular segment pointing generally perpendicular to the central axis of the first tubular segment.

11. The method of claim 9, wherein the attaching forms a connection between the first tubular segment and the second tubular segment such that the connection generally prevents blood flow through the connection.

12. The method of claim 9, further comprising cutting the proximal end of the second tubular segment at an angle of between zero to 90 degrees to prepare it for connection to the first tubular segment.

13. The method of claim 9, further comprising packaging the vascular bypass graft in a container containing the vascular bypass graft and preservative solution.

14. The method of claim 13, wherein the container containing the vascular bypass graft is also frozen or chilled.

15. The method of claim 9, wherein one or more of the first tubular segment and the second tubular segment are constructed from human or animal donor, bioengineered or derived from polymers.

* * * * *